United States Patent [19]

McCullough et al.

[11] Patent Number: 4,753,254

[45] Date of Patent: Jun. 28, 1988

[54] METHOD AND APPARATUS FOR A DENTAL FLOSS SYSTEM

[76] Inventors: Edward E. McCullough; Kevin W. McGaha, both of P.O. Box 46, Brigham City, Utah 84302

[21] Appl. No.: 90,116

[22] Filed: Aug. 27, 1987

[51] Int. Cl.$^4$ .............................................. A61C 15/00
[52] U.S. Cl. ...................................................... 132/90
[58] Field of Search ........................ 433/89, 90, 91, 92

[56] References Cited

U.S. PATENT DOCUMENTS 3,474,799 10/1969 Cappello .............................. 132/90

Primary Examiner—Robert Peshock
Attorney, Agent, or Firm—Edward E. McCullough

[57] ABSTRACT

A method and apparatus for a dental floss system is disclosed, using an applicator having two resilient prongs on one end of a handle member and floss having nodules fixed thereto and spaced apart at distances shorter than the relaxed distance between the prongs of the applicator. The prongs have small shoulders on their ends with slots passing through the ends including the shoulders, so that floss can be loaded into the slots and the nodules thereon trapped behind the shoulders to retain the floss on the applicator. The floss is loaded onto the applicator by moving the prongs between two converging surfaces that hold a span of the floss in slots. This compresses the prongs together until the span of floss is intercepted by the slots in the ends of the prongs. The prongs are then removed from the convergent surfaces, whereupon they tend to spring into their relaxed positions, retaining the floss by trapping two of the adjacent nodules thereon behind the shoulders on the prongs. The second span of floss that lies between the following two nodules is then loaded into the slots of the convergent surfaces. The floss is then cut by a raised cutting tab on the surface of the floss container. The further functional nodule, relative to the position of the cutting tab determines the exact location at which the floss is cut.

34 Claims, 1 Drawing Sheet

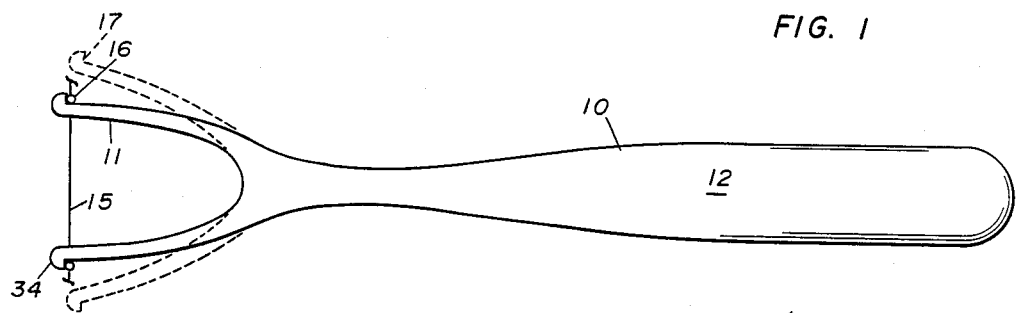
FIG. 1
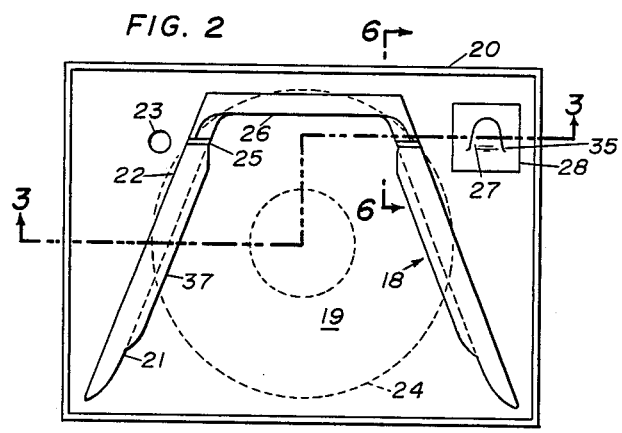
FIG. 2
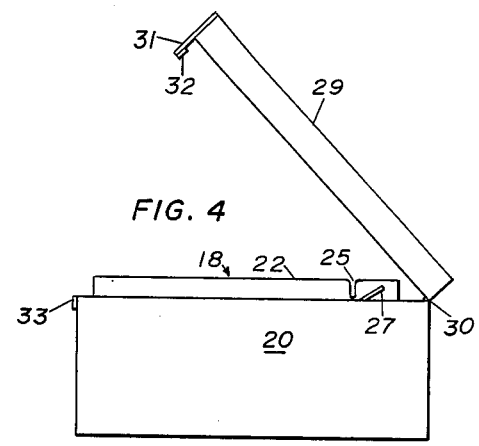
FIG. 4
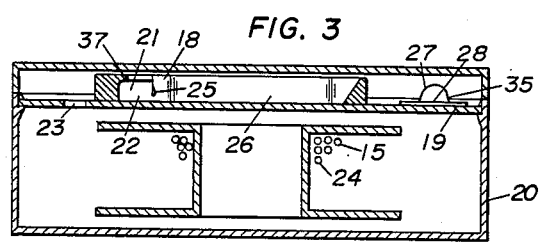
FIG. 3
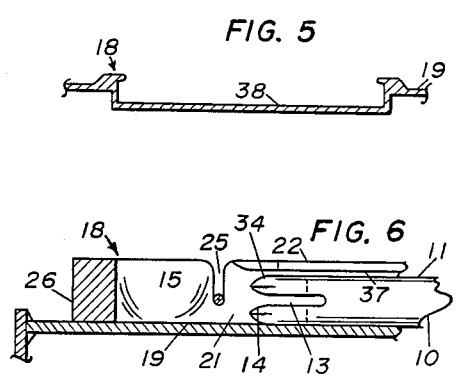
FIG. 5
FIG. 6
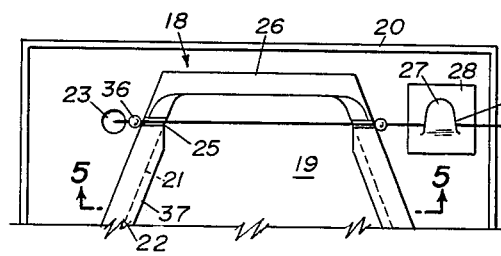
FIG. 7
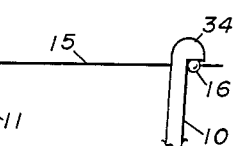

METHOD AND APPARATUS FOR A DENTAL FLOSS SYSTEM

CROSS REFERENCES TO RELATED APPLICATIONS

This application is related to the following applications filed simultaneously herewith: "Dental Floss Applicator," Ser. No. 07/090115, filed 8/25/87, by Edward E. McCullough and Kevin W. McGaha; and "Dental Floss Applicator" (design) Ser. No. 07/090139, filed 8/27/87, by Edward E. McCullough.

BACKGROUND OF THE INVENTION

1. Field of the invention:

This invention relates to methods and apparatus for promoting dental hygiene by applying dental floss to the teeth of the user. More specifically, it relates to methods and apparatus for loading dental floss onto an applicator having a pair of resilient prongs by means of nodules on the floss, slots in the ends of the prongs for holding the floss, and convergent surfaces for compressing the prongs together.

2. Description of the prior art:

Dental floss having nodules fixed thereto at intervals is known in the prior art, as are applicators having resilient prongs for holding the floss by means of bearing outwardly against two adjacent nodules on the floss. Examples of such systems are shown in U.S. Pat. No. 1,815,408 "Dental Floss Holder" to J. K. Jordan, and 3,631,869 "Dental Floss Holder" to R. J. Espinosa. A similar device is shown in U.S. Pat. No. 4,162,687 "Dental Flossing Device" to L. C. Lorch. In this patent, the flossing material is made in short segments, each of which has a small, circular grommet that fits over a knob at the end of each prong of the applicator. German Pat. No. 1095460 to Gustav Frantz is also somewhat similar to the first two patents cited above. However, in this patent, tension on a segment of floss is achieved by a collar surrounding both prongs at a point at which they are disposed at and angle to one another, so that, by sliding the collar along the prongs, they can be positioned at a desired distance from one another.

Other U.S. patents, known to the applicant, that show dental-floss holders, but which are fairly unrelated to the present invention are: U.S. Pat. Nos. 4,253,477; 3,828,804; 2,702,555; 3,974,842; and 4,052,994.

SUMMARY OF THE INVENTION

A difficulty experienced when using dental-floss systems of the type described in U.S. Pat. No. 1,815,408 to Jordan is that loading the floss material onto the applicator is somewhat awkward. Ideally, the user must have three hands—one for holding the floss supply, one for holding the applicator and compressing its prongs together, and a third for loading a segment of floss onto the prongs of the applicator. While most normal adults should be able to learn to juggle such devices effectively, it can be a problem for children and for individuals with impaired manual skills, e.g. arthritic hands. Of course, not having to acquire special skills in order to operate a simple device is appreciated by everyone.

The present invention is directed primarily toward overcoming this difficulty in the prior art. Therefore, it is an object of the invention to provide a method and apparatus for loading a segment of dental floss conveniently and easily onto an applicator. Another object of the invention is to provide an apparatus thereof that is simple in construction and without moving parts—which enhances its reliability. Another object of the invention is to provide apparatus that is simple in form, so that it can be easily cleaned and maintained in a sanitary condition. Another object of the invention is to provide a method of loading a segment of dental floss onto an applicator that is convenient and easily accomplished.

The apparatus of the invention is essentially a loading device for an applicator, adapted for use therewith, having a pair of resilient prongs for holding dental floss and a dental floss having nodules fixed thereto at intervals.

The method of the invention consists essentially of the procedure by means of which the applicator and loading device cooperate in loading a segment of the floss onto the applicator.

Other objects and advantages of the invention will become apparent as the following, detailed description is read with reference to the accompanying drawings. The part numbers refer to the same parts throughout the disclosure.

BRIEF DESCRIPTION OF THE DRAWINGS

In the drawings:

FIG. 1 is a top view of an applicator of the type used in the present invention;

FIG. 2 is a top view of the apparatus of the invention without its cover lid;

FIG. 3 is sectional view taken on line 3—3 of FIG. 2, but including the cover lid;

FIG. 4 is a side view of the apparatus;

FIG. 5 is a fragmentary sectional view of a second embodiment of the upper surface of the floss container, wherein it is recessed between the convergent surfaces;

FIG. 6 is a fragmentary sectional view taken on line 6—6 of FIG. 2 and including portions of floss and the applicator to show their relative positions during the loading process;

FIG. 7 shows a portion of FIG. 2, to illustrate how the floss is automatically measured by a nodule thereon for cutting in a desired location, and how it is loaded into the prongs of an applicator.

DETAILED DESCRIPTION OF THE PREFERRED EMBODIMENTS

The present invention uses an applicator 10 of the type shown in U.S. Pat. No. 1,815,408, cited above, wherein two resilient, juxtaposed prongs 11 are fixed to an elongated handle 12, as shown in FIG. 1. The outward-end portion of each prong 11 has a small slot 13 for receiving and holding dental floss. The slots 13 lie in the plane of the two prongs 11. Although applicators of this type are known in the prior art, the applicator shown in FIG. 1 is especially adapted in form and dimensions for use with the apparatus of the present invention.

The floss material 15 is also of a type shown in U.S. Pat. No. 1,815,408, wherein knots or nodules 16 of a rigid material are fixed at intervals to the floss 15 (See FIGS. 1 and 7). The distance between adjacent pairs of nodules 16 that are loaded simultaneously on an applicator 10 must be less than the relaxed distance between the prongs 11 of the applicator 10; so that, when the floss 15 is loaded onto the applicator 10, each of the prongs 11 will bear outwardly against a nodule 16 for retention of the floss 15 on the prongs 11.

For convenience and clarity in the following description and claims: "Functional pair" shall refer to two adjacent nodules 16 on the floss 15 that define the appropriate length of floss that can be loaded onto the applicator 10 effectively (i. e. a span somewhat shorter than the relaxed distance between the prongs 11); and "Functional span" shall refer to the length of floss 15 between two functional pairs of nodules 16. It can be seen that there may be advantages in manufacturing the floss 15 so that the distance between functional pairs of nodules 16 is not the same length as a functional span of the floss 15. For example, floss could be conserved by making this distance shorter than a functional span. However, for the purposes of the present invention, for ease of manufacture and convenience in use, it is preferred that all of the nodules 16 be equally spaced apart on the floss 15.

Retention of the floss 15 on the prongs 11 is made secure by a small, outwardly-extending shoulder 17 on each prong 11, positioned slightly forward of the inner end of its corresponding slot 13, so that each slot 13 passes through its shoulder 17. When a functional span of floss 15 is loaded into the slots 13, each one of the functional pair of nodules 16 on the floss 15 becomes trapped behind its respective shoulder 17. Because of the tension on the loaded floss 15 imposed by the resilient prongs 11, the trapped nodules are unable to move in any direction.

The floss-loading device 18 is preferably built on the upper surface 19 of a floss container 20, best shown in FIGS. 2 and 3. It comprises two elongated, convergent surfaces 21, which are preferably the inner surfaces of two elongated members 22 that are fixed to the upper surface 19 of the floss container 20. As shown in FIG. 3, the members 22 are approximately rectangular in cross section. However, this shape could be triangular or any other suitable form. Alternatively, the space between the surfaces 21 could be a depression 38 in the upper surface 19 and, hence, these surfaces 21 could, at least partially, be formed by the walls of the depression 38 (See FIG. 5). Nevertheless, it is preferable that the surfaces 21 be substantially perpendicular to the upper surface 19 of the container 20.

An opening 23 permits floss 15 to pass through the upper surface 19 of the container 20 from a supply 24 of floss 15 inside the container 20.

A pair of slots 25 is located in the members 22 near the convergent ends thereof. These slots 25 are preferably perpendicular to the surface 19 and are open to the upper edges of the members 22. The lower ends of the slots 25 are substantially the same distance from the upper surface 19 of the container 20 as are the lower edges of the slots 13 in the prongs 11 when the prongs are in contact with the surface 19 and in a position to intercept a segment of floss supported in the slots 25. This correlation of the measurements of the slots 25 and the slots 13 relative to the upper surface 19 of the container 20 is necessary to insure loading of the floss 15 in the slots 13 of the applicator 10.

A stop member 26 is located at the convergent ends of the elongated members 22. It is preferably a plate fixed perpendicular to the upper surface 19 of the container 20 and joining the two convergent ends of the elongated members 22. The purpose of this member 26 is to stop the forward motion of the applicator 10 after it has fully grasped a span of the floss 15 (i. e., when the floss has reached the innermost ends of the slots 13). Hence, it could have many forms other than the plate 26. It could be projections or pegs extending upward from the surface 19 adjacent and inside the convergent ends of the surfaces 21, or extending from those surfaces, themselves; or it could be in the form of two short flanges extending inwardly from the convergent surfaces 21.

A raised metal tab 27 is fixed to the upper surface 19 of the container 20 on the opposite side of the convergent members 22 relative to the opening 23. This tab 27 is a well-known feature of dental-floss containers, used for cutting the floss. It may be a part of a small metal plate 28 that is glued or otherwise fixed to the surface 19. In the present invention, its location on the upper surface of the container 20 is important in order that it may cooperate with the other elements of the invention to permit one-handed loading and cutting of the floss 15 with the applicator 10.

The container 20 is preferably equipped with a cover lid 29 that is hinged at one edge to the top of the container 20 (See FIG. 4). While the edge of the container to which it is hinged is optional, the preferred edge for the hinge 30 is the edge adjacent the convergent ends of the elongated members 22. This minimizes interference of the lid 29 with the process of loading floss 15 onto the applicator 10. The present invention employs the common method of hinging lids and the like to plastic containers, which comprises making the lid 29 integral with the remainder of the container 20 but achieving the required flexibility for hinging action simply by making the hinge portion 30 thinner than the lid 29 or the walls of the container 20. The invention also employs a common method of latching the lid 29 to the container 20, which comprises a small tab 31 extending downward from the lid 29 on the edge thereof opposite the hinge 30. A small, inwardly-extending projection 32 fixed to the latch tab 31 slides over an outwardly-extending projection 33 on the outside of the container 20 when the lid 29 is closed. The projection 33 thereafter tends to retain the lid 29 in a closed position relative to the container 20.

When practicing the invention, the user first opens the lid 29 and pulls a length of floss 15 containing two functional nodules 16 through the opening 23. This floss is then placed in the slots 25 in the elongated members 22 so that each of the nodules 16 rests on the outside surface of its respective member 22. He then places the end portions 34 of the prongs 11 between the divergent ends of the convergent surfaces 21 and in contact with the upper surface 19 of the container 20, so that the slots 13 in the prongs 11 are substantially parallel to the surface 19 (See FIGS. 6 and 7). Maintaining this attitude, the prongs 11 are then moved forwardly toward the convergent ends of the surfaces 21 until stopped by the stop member 26. At this point, the span of floss 15 supported in the slots 25 has been fully passed into the slots 13 in the ends of the prongs 11. The user then lifts the prongs 11 from between the convergent surfaces 21, whereupon, they spring outwardly and trap the two nodules 16 behind the shoulders 17 on the ends of the prongs 11, By moving the applicator 10 slightly, a further length of floss 15 containing a second set of functional nodules 16 is pulled through the opening 23. This second functional span of floss 15 is loaded into the slots 25 in the same manner as was the first span—with the nodules 16 being placed outside the elongated members 22. By another slight movement of the applicator 10, the floss 15 is passed under the cutting tab 27 and severed. The loaded span of floss is then applied to the teeth of the user by means of the applicator 10. When the user is ready for a second span of the floss 15, the prongs 11 are compressed together manually, the used floss removed, and the above procedure for loading the floss 15 is repeated.

The tab 27 is positioned on the surface 19 of the container 20 so that its cutting edge 35 severs the floss 15 between functional pairs of nodules 16 when the second functional span of floss 15 is loaded in the slots 25 of the convergent members 22. In this way, the further nodule 36, relative to the cutting tab 27, functions as a stop means to prevent further movement of the floss 15 when the floss between the applicator 10 and the further nodule 16 becomes taught. In this way, the further nodule 36 becomes a measuring device to determine automatically where the floss 15 is to be cut.

A preferred form of the invention includes a small, inwardly projecting lip 37 at the upper edge of each elongated member 22 that extends from its divergent end to its slot 25. This feature assists in retaining the applicator prongs between the convergent surfaces 21 during their forward motion toward the supported span of floss 15 to insure that the floss 15 is grasped in the slots 14 of the applicator 10. It can be seen that other forms can perform the function of the lip 37, such as a short, inwardly-extending flange or the convergent surfaces 21 can be somewhat upwardly convergent.

Also, the portion of each elongated surface 21 between its slot 25 and its convergent end is upwardly divergent and curved to conform to the shape of the end portions of the prongs 11. This feature allows the prongs 11 to spring outwardly and automatically eject from between the elongated surfaces 21 when the floss 15 has been loaded into the applicator prongs.

An invention has been described that advances the art of dental hygiene. Although the embodiments thereof have been described in considerable detail, it should be noted that many such details may be altered without departing from the scope of the invention, as it is defined in the following claims.

We claim:

1. The method of loading dental floss onto an applicator comrpising the steps of:
   interposing the prongs of an applicator, having a pair of resilient prongs with slots in the ends thereof between the divergent ends of two juxtaposed, convergent surfaces so that each of said prongs contacts a different one of said surfaces and so that forward movement of said prongs is in the direction of convergence thereof, whereby said prongs are compressed toward each other;
   orienting said slots so that they lie in a common plane with the directional vector of said forward movement of the prongs between the convergent surfaces;
   placing dental floss, having a functional pair of nodules fixed to the floss and spaced apart thereon, in front of said prongs and in the plane of said slots so that the functional span of floss between said nodules spans said convergent surfaces with each of said nodules lying outside its corresponding convergent surface;
   moving the prongs with said forward movement between said surfaces until said floss is automatically engaged in said slots of the prongs; and
   lifting the prongs form between the convergent surfaces so that the prongs tend to spring into their normal, uncompressed positions and bear outwardly against said nodules.

2. The method of claim 1 further including the step of providing a third surface perpendicualr to said convergent surfaces and fixed thereto, and wherein the step of moving said prongs forwardly between the convergent surfaces is performed with the prongs in contact with said third surface, whereby said third surface can function as a guide to direct said prongs with precision toward said functional span of floss.

3. The method of claim 2 further including the step of providing two opposing slots in said convergent surfaces for holding said span of floss, said slots being perpendicular to said third surface and each having a closed end adjacent said third surface and an open end.

4. The method of claim 3 including the steps of making the distance from said clsoed ends of said slots to said third surface and the distance from said slots in said prongs to said third surface approximately equal when the prongs are in contact therewith and in an attitude to grasp said floss, so that moving the prongs forwardly automatically causes said span of floss to be engaged in said slots of the prongs when said floss is in said closed ends of the slots in the convergent surfaces.

5. The method of claim 4 further including the step of expanding outwardly the open-end portion of each of said slots in said prongs to facilitate intercepting said floss therein.

6. The method of claim 3 further including the steps of: fixing a continuous series of functional pairs of said nodules on a continuous strand of said floss; loading a second functional span of said floss into the slots of said convergent surfaces when said first functional span of floss has been loaded into said slots of the prongs; and cutting the floss between the two functional spans of floss.

7. The method of claim 6 further including the step of positioning a cutting edge a fixed distance from the further nodule of said second span of floss, relative to said first span, and wherein said step of cutting the floss is performed on said cutting edge, so that said further nodule functions as a measuring device to determine automatically where said floss is cut.

8. Apparatus for loading dental floss, that has spaced-apart nodules fixed theron, onto an applicator having two juxtaposed, resilient prongs attached to a handle, each prong having a slot in its outer-end portion for receiving and retaining the floss, comprising: two juxtaposed, elongated surfaces, perpendicular to a common plane with two ends thereof converging toward one another, so that each of said elongated surfaces has an upper edge, a lower edge, a convergent end and a divergent end; means for supporting said convergent surfaces in fixed relationship to one another; and means for supporting a functional span of said floss in a position to be grasped in the slots of said prongs by forward movement thereof between said convergent surfaces.

9. The apparatus of claim 8 wherein said means for supporting the elongated surfaces relative to one another is a third surface to which each of said convergent surfaces is perpendicularly fixed at its lower edge.

10. The apparatus of claim 9 wherein the convergent surfaces are the opposing, innner surfaces of two elongated members fixed to said third surface.

11. The apparauts of claim 9 wherein the portion of said third surface that lies between said convergent surfaces is recessed, so that the convergent surfaces are at least partially the surfaces of the walls of said recess.

12. The aparatus of claim 8 wherein said means for supporting a functional span of dental floss comprises a slot formed in each of said convergent surfaces directly opposite one another and spaced from the divergent end of said elongated surfaces such that the prongs of an applicator moving between them are compressed so that the distance between said prongs is less than that between functional nodules of said floss, said slots being approximately perpendicular to said third surface and each having an upper end open to the upper edge of its corresponding convergent surface and a lower end.

13. The apparatus of claim 12 further including means for stopping further forward movement of said prongs between said convergent surfaces when said slots of said prongs have fully grasped said span of dental floss supported in said slots of the convergent surfaces.

14. The apparatus of claim 13 wherein said stop means comprises a plate fixed perpendicular to said third surface and adjoining said convergent ends of the convergent surfaces, said plate being approximately the same distance from the slots in the convergent surfaces as the length of the slots in said prongs, whereby forward movement of said prongs between said convergent surfaces is stopped when said supported span of floss is fully grasped in the slots of the prongs.

15. The apparatus of claim 12 wherein said lower end of each of said slots is approximately the same distance from the third surface are siaid slots in the prongs of said applicator when the prongs of the applicator are placed between said convergent surafaces, in contact with said third surface, and with the slots of said prongs parallel to said third surface in an attitude to grasp said floss.

16. The apparatus of claim 12 wherein said convergent surfaces, between said slots in said surfaces and the convergent ends thereof, are divergent toward their upper edges so that prongs of said applicator are ejected upwardly from between said surfaces after the prongs have fully grasped a span of floss supported in said slots.

17. The apparatus fo claim 12 further including a small, inwardly-extending lip on the upper edge of each of said convergent surfaces between the divergent end thereof and said slot in said surface, for retaining resilient prongs of an applicator between the convergent surfaces until the prongs have fully grasped a span of floss being supported in said slots.

18. The apparatus of claim 9 further including a container for dental floss comprising an enclosure having an upper surface and defining an opening in the container through which dental floss can be passed, and wherein said third surface of said loading apparatus comrises the upper surface of said enclosure.

19. The apparatus of claim 18 wherein said opening is in the upper surface of the container and on one side of said pair of convergent surfaces.

20. The apparatus of claim 19 further including means for cutting dental floss.

21. The apparatus of claim 20 wherein said means for cutting floss comprises a cutting tab fixed to said upper surface of said container and positioned thereon so that when a functional span of said floss is loaded in said slots, with each of the functional nodules outside its respective convergent surface, the cutting edge of said tab will sever the floss between functional pairs of nodules when said floss is passed thereunder with slight tension on the floss, whereby the further nodule of the floss loaded in the convergent surfaces, relative to the position of the cutting edge, becomes a measuring device for determining the location at which the floss is cut.

22. A dental-floss container comprising:
an enclosure having a substantially flat upper surface;
a pair of elongated surfaces, each having an upper edge, and a lower edge fixed to said upper surface so that the elongated surfaces are perpendicular thereto, and being in a juxtaposed, convergent relationship to one another so that said pair has a convergent end and a divergent end;
means for supporting a functional span of dental floss parallel to said upper surface so that it extends from one said convergent surface to the other at a location between ends of said surfaces wherein the distance between them is shorter than a functional span of saidi floss, wherein said floss is of the type having pairs of nodules fixed thereto and spaced apart to define functional spans of floss between them; and
structure defining an opening in said upper surface adjacent said pair of convergent surfaces, through which floss may pass.

23. The container of claim 22 wherein said elongated surfaces are the opposing, inner surfaces of a pair of juxtaposed, elongated members fixed to said upper surface of the container.

24. The container of claim 22 wherein said means for supporting a span of siad floss comprises structure forming a slot in each of said convergent surfaces adjacent the convergent end thereof, each slot having an open end at the upper edge of its corresponding convergent surface and a lower end adjacent said upper surface of the container, and each said slot being substantially perpendicular to said upper surface, said slots being wide enough to admit passage therein of said floss but not wide enough for passage therethrough of said nodules, so that a span of said floss can be supported in said second slots and be prevented from lateral movement by a functional pair of said nodules, each being outside its respective convergent surface.

25. The container of claim 24 wherein said convergent surfaces are upwardly divergent between said slots in said surfaces and the convergent ends thereof, so that prongs of an applicator are automatically ejected upwardly from between the convergent surfaces after the prongs have grasped a span of floss being supported in said slots.

26. The container of claim 24 further including a small, inwardly-extending lip on the upper edge of each of said convergent surfaces between the divergent end thereof and said slot in said surface for retaining the prongs of an applicator between the convergent surfaces until the prongs have fully grasped a span of floss being supported in said slots.

27. The container of claim 24 further including means for cutting dental floss.

28. The container of claim 27 wherein said means for cutting floss comprises an upraised tab having a sharp cutting edge and fixed to said upper surface.

29. The container of claim 28 wherein said sharp edge of said tab is positioned on said upper surface of the container so that, when a first functional span of said floss is loaded in the prongs of an applicator and a second functional span of floss is loaded in the slots of said convergent surfaces, with each of the nodules outside its respective convergent surface, said cutting edge will sever the floss between functional pairs of nodules when said floss is passed thereon with tension on the floss.

30. The container of claim 20 further including means for stopping prongs of a dental floss aplicator that is being moved between said convergent surfaces toward the convergent end thereof and in contact with said upper surface when they have fully grasped said supported span of dental floss.

31. The container of claim 30 wherein said stop means comprises a plate fixed perpendicular to said upper surface of the container and extending from one convergent end to the other of said elongated surfaces.

32. The container of claim 22 further including a supply of dental floss within said enclosure, said floss having nodules fixed thereto and spaced apart to provide pairs of adjacent nodules that define functional spans of floss between them.

33. The container of claim 23 further including a protective cover that fits over said upper surface and is attached to said container at one edge thereof by a hinge.

34. The container of claim 33 further including means opposite said hinge for temporarily fastening said protective cover to said container.

* * * * *